(12) United States Patent
Bartlett et al.

(10) Patent No.: US 7,071,222 B2
(45) Date of Patent: Jul. 4, 2006

(54) PREPARATION CONTAINING A COMBINATION OF 5-METHYLISOXAZOLE-4-CARBOXYLIC ACID-(4-TRIFLUOROMETHYL)-ANILIDE AND N-(4-TRIFLUOROMETHYLPHENYL) 2-CYANO-3-HYDROXYCROTONIC ACID AMIDE

(75) Inventors: Robert Bartlett, Darmstadt (DE); Johann Then, Frankfurt (DE)

(73) Assignee: Sanofi-Aventis Deuschland GmbH, Frankfurt am Main (DE)

( * ) Notice: Subject to any disclaimer, the term of this patent is extended or adjusted under 35 U.S.C. 154(b) by 878 days.

(21) Appl. No.: 09/101,672

(22) PCT Filed: Mar. 7, 1997

(86) PCT No.: PCT/EP97/01167

§ 371 (c)(1),
(2), (4) Date: Oct. 23, 1998

(87) PCT Pub. No.: WO97/34600

PCT Pub. Date: Sep. 25, 1997

(65) Prior Publication Data

US 2002/0006945 A1   Jan. 17, 2002

(30) Foreign Application Priority Data

Mar. 20, 1996   (DE) ................ 196 10 955

(51) Int. Cl.
*A61K 31/42*      (2006.01)
*A61K 31/275*   (2006.01)

(52) U.S. Cl. .................................... 514/378; 514/521
(58) Field of Classification Search ................ 514/378, 514/521
See application file for complete search history.

(56) References Cited

U.S. PATENT DOCUMENTS

| | | | | |
|---|---|---|---|---|
| 4,965,276 A | * | 10/1990 | Bartlett et al. | 514/378 |
| 5,268,382 A | | 12/1993 | Bartlett et al. | 514/521 |
| 5,494,911 A | | 2/1996 | Bartlett et al. | 514/256 |
| 5,532,259 A | | 7/1996 | Bartlett et al. | 514/378 |
| 5,679,709 A | | 10/1997 | Bartlett et al. | 514/521 |
| 5,728,721 A | | 3/1998 | Bartlett | 514/378 |
| 6,303,792 B1 | | 10/2001 | Lau et al. | |

FOREIGN PATENT DOCUMENTS

| | | |
|---|---|---|
| DE | 41 27 737 A1 | 2/1993 |
| EP | 0 217 206 A2 | 4/1987 |
| EP | 0 665 013 A1 | 8/1995 |
| WO | WO 91/17748 | 11/1991 |

* cited by examiner

*Primary Examiner*—James O. Wilson
*Assistant Examiner*—Everett White
(74) *Attorney, Agent, or Firm*—Finnegan, Henderson, Farabow, Garrett and Dunner, L.L.P.

(57) ABSTRACT

A solid composition comprising 5-methyl-4'-trifluoromethyl-4-isoxazole carboxanilide and N-(4-trifluoromethylphenyl)-2-cyano-3-hydroxycrotonic acid amide, suitable for treatment of immunological and cancerous diseases.

14 Claims, No Drawings

PREPARATION CONTAINING A COMBINATION OF 5-METHYLISOXAZOLE-4-CARBOXYLIC ACID-(4-TRIFLUOROMETHYL)-ANILIDE AND N-(4-TRIFLUOROMETHYLPHENYL) 2-CYANO-3-HYDROXYCROTONIC ACID AMIDE

DESCRIPTION

Combination preparation, comprising 5-methyl-4'-trifluoromethyl-4-isoxazolecarboxanilide and N-(4-trifluoromethylphenyl)-2-cyano-3-hydroxycrotonamide The European Patent Application with the publication number 0 013 376 disclosed that 5-methyl-4'-trifluoromethyl-4-isoxazolecarboxanilide (compound 1) has antirheumatic, antiinflammatory, antipyretic and analgesic activity and can be employed against multiple sclerosis. Pharmaceuticals which comprise the active compound 5-methyl-4'-trifluoromethyl-4-isoxazolecarboxanilide are administered orally in doses of from 25 mg to 150 mg.

The European Patent Application with the publication number 0 217 206 reports that N-(4-trifluoromethylphenyl)-2-cyano-3-hydroxycrotonamide (compound 2) has immunomodulating properties and is suitable for treating chronic graft-versus-host disease and autoimmune diseases, in particular systemic lupus erythematosus. Pharmaceutical preparations which comprise a compound 1 or compound 2 can be administered in a dose of from 10 to 200 mg, preferably, however, of from 50 to 100 mg, in the case of an injection solution in ampoule form (intravenous), in particular based on compound 2 or a salt thereof, of from 1 to 30 mg, preferably of from 5 to 10 mg, and, in the case of rectal administration, of from 50 to 300 mg, preferably of from 100 to 200 mg. However, the oral administration of 5 mg or 10 mg of compound 1 or compound 2, in each case on its own, per kg does not have any significant effect.

It has been found that a combination preparation, which comprises compounds 1 and 2, exhibits surprisingly advantageous immunosuppressive effects. The addition of small quantities of compound 2 to the main active component compound 1 results in a marked increase in the activity of the combination preparation. Due to the magnitude of this effect, the use of this combination can be extended to areas which hitherto remained closed to an immunosuppressive therapy using the individual components. Furthermore, the reduction in the dose, without any decreased activity, leads to greater safety in use. At the same time, it can be assumed that a reduction in the dose in association with unchanged activity will enable the therapy costs to be lowered substantially.

The invention relates, therefore, to a solid preparation which comprises component 1) 5-methyl-4'-trifluoromethyl-4-isoxazolecarboxanilide, component 2) N-(4-trifluoromethylphenyl)-2-cyano-3-hydroxycrotonamide and/or a physiologically tolerated salt of N-(4-trifluoromethylphenyl)-2-cyano-3-hydroxycrotonamide and/or a stereoisomeric form of N-(4-trifluoromethylphenyl)-2-cyano-3-hydroxycrotonamide and 3) a pharmaceutical excipient, wherein the content of component 1 is from 2 to 20 mg and the content of component 2) is from 0.3% to 50% of that of component 1).

The compounds 5-methyl-4'-trifluoromethyl-4-isoxazolecarboxanilide and N-(4-trifluoromethylphenyl)-2-cyano-3-hydroxycrotonamide can be produced using known methods (EP 0 529 500). N-(4-Trifluoromethylphenyl)-2-cyano-3-hydroxycrotonamide having the following structural formula

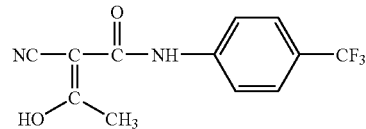

is employed as such and/or a physiologically tolerated salt of N-(4-trifluoromethylphenyl)-2-cyano-3-hydroxycrotonamide and/or a stereoisomeric form of N-(4-trifluoromethylphenyl)-2-cyano-3-hydroxycrotonamide in the preparation according to the present invention.

Examples of suitable physiologically tolerated salts of N-(4-trifluoromethylphenyl)-2-cyano-3-hydroxycrotonamide are alkali metal, alkaline earth metal or ammonium salts, including those of physiologically tolerated organic ammonium bases.

The novel solid preparation is suitable, for example, for treating
  acute immunological events, such as sepsis, allergy and graft-versus-host reactions and host-versus-graft reactions
  autoimmune diseases, in particular rheumatoid arthritis, systemic lupus erythrematosus and multiple sclerosis
  psoriasis, atopic dermatitis, asthma, urticaria, rhinitis and uveitis
  type II diabetes
  hepatic fibrosis, cystic fibrosis and colitis
  cancerous diseases, such as lung cancer, leukemia, ovarian cancer, sarcoma, Kaposi's sarcoma, meningioma, intestinal cancer, lymph node cancer, brain tumours, breast cancer, pancreatic cancer, prostate cancer or skin cancer.

The novel solid preparation can also comprise combination packs or compositions, in which the components are juxtaposed and can therefore be administered simultaneously, separately or at graded time intervals to one and the same human or animal body. According to the invention, components 1 and 2 can also be present in juxtaposed, separate medicinal forms, in particular when the spatial dimensions of the medicinal forms make administration more difficult. This applies, in particular, to the oral forms, since elderly patients often have an aversion to large tablets or capsules. It is imperative that the separate, juxtaposed medicinal forms are arranged so that they can be taken at the same time. In this context, different forms, for example a tablet and a capsule, can also be present alongside each other.

The invention furthermore relates to the use of a combination of compounds 1 and 2 for preparing a pharmaceutical which exhibits a hyperadditive increase in the immunosuppressive effect.

The invention furthermore relates to a process for producing the novel preparation, wherein compounds 1 and 2 and a pharmaceutical excipient are processed into a pharmaceutical administration form.

The novel solid preparation can be present as a dosage unit in the form of medicinal forms such as capsules (including microcapsules), tablets (including coated tablets and pills) or suppositories, with it being possible, when capsules are used, for the capsule material to exercise the function of the excipient and the content to be present, for example, as a powder, gel, emulsion, dispersion or solution. However, it is particularly advantageous and simple to prepare oral (peroral) formulations with the two compounds 1 and 2, which formulations comprise the calculated quantities of the active compounds together with each desired pharmaceutical excipient. A corresponding formulation (suppository) for rectal therapy can also be used. Transdermal administration in the form of ointments, creams or oral administration of solutions which comprise the novel preparation, is likewise possible.

In addition to the active compounds, ointments, pastes, creams and powders can also comprise the customary excipients, for example animal and vegetable fats, waxes, paraffins, starch, tragacanth, cellulose derivatives, polyethylene glycols, silicones, bentonites, talc, zinc oxide, lactose, silicic acid, aluminum hydroxide, calcium silicate and polyamide powders, or mixtures of these compounds.

The tablets, pills or granulate bodies can be prepared by customary processes, such as compressing, dipping or fluidized bed processes or boiler coating, and comprise excipients and other customary auxiliary substances such as gelatin, agarose, starch (e.g. potato, corn or wheat starch), cellulose, such as ethyl cellulose, silicon dioxide, various sugars, such as lactose, magnesium carbonate and/or calcium phosphates. The coating solution is normally composed of sugar and/or corn syrup and usually also contains gelatin, gum arabic, polyvinylpyrrolidone, synthetic cellulose esters, surface-active substances, plasticizers, pigments and similar additives corresponding to the state of the art. Any customary flowance agent, lubricating agent or glidant, such as magnesium stearate and mold lubricant can be used for producing the preparations.

Preferably, the preparations are in the form of casing/core tablets or multilayer tablets, with compound 2 being located in the casing or in the core or in a layer, while compound 1 is located in the core or in the casing or in another layer. Compounds 1 and 2 can also be present in delayed-release form, or be adsorbed to release-delaying material or be enclosed in the release-delaying material (for example material of this kind based on cellulose or polystyrene resin, for example hydroxyethyl cellulose). Delayed release of the active compounds can also be achieved by providing the layer in question, or the compartment, with customary coatings which are insoluble in gastric juice.

The dose to be used naturally depends on different factors, such as the living subject (i.e. human or animal) to be treated, age, weight, general state of health, the severity of the symptoms, the disease to be treated, any accompanying diseases, (if present) the nature of the accompanying treatment with other pharmaceuticals, or the frequency of the treatment. In general, the doses are administered several times daily and preferably from once to three times daily. In this context, the quantities of individual active compound which are used are based on the recommended daily dose of the particular individual active compound and should, in the combination preparation, generally be from 10% to 100% of the recommended daily dose, preferably from 20% to 80%, in particular 50%. The appropriate therapy with the novel combinations consequently comprises, for example, the administration of one, two or 3 individual doses of the preparation composed of 1) 5-methyl-4'-trifluoromethyl-4-isoxazolecarboxanilide in a quantity of from 2 to 20 mg, 2 to 19.9 mg, 4.5 to 19.5 mg, 4.85 to 19 mg, 5 to 18 mg, 5 to 15 mg, 5 to 10 mg, 5 to 9.9 mg, 5 to 9.7 or 5 to 9.0 mg and
2) N-(4-trifluoromethylphenyl)-2-cyano-3-hydroxycrotonamide in a quantity of from 0.3% to 50%, preferably of from 0.5% to 20%, in particular of from 0.8% to 15%, particularly preferably of from 1% to 10%, very particularly preferably of from 1% to 5%; in each case based on the content of 5-methyl-4'-trifluoromethyl-4-isoxazolecarboxanilide, and
3) a pharmaceutically tolerated excipient.

The percentage values (%) of compounds 1 and 2 refer in each case to percent by weight.

The quantities of the active components naturally depend on the number of individual doses and also on the disease to be treated. The individual dose can also be composed of several dosage units which are administered simultaneously.

EXAMPLE 1

Pharmacological Tests

Adjuvant-induced arthritis, modification in accordance with Perper (Proc. Soc. exp. Biol. Med. 137, 506 (1971))

Male rats of a Lewis strain (Moellegard, Denmark) having a body weight of from 160 to 210 g are used as the experimental animals. On the 1st day, the animals are injected subcutaneously, into the tail root, with complete Freund's adjuvant containing a suspension of Mycobacterium butyricum in heavy paraffin oil (Difco; 6 mg/kg in paraffin oil; Merck). Compounds 1 and 2 are suspended in carboxymethyl cellulose (1% in water) and this suspension is administered orally. The compounds are administered once daily from the 1st to the 12th day of the experiment. The paw volume and the arthritis index are determined on the 18th day.

The severity of the disorder is determined by measuring the volumes of both hind paws. The measurement is carried out by the water displacement method, using a 2060 plethysmometer (Rhema-Labortechnik, Hofheim, Germany). In addition, the arthritis index is determined on the 18th day after injection.

| Determination of the arthritis index: | |
|---|---|
| 1. Ears | 0.5 point for each ear on which redness appears and nodules are formed |
| 2. Nose | 1 point for connective tissue swelling |
| 3. Tail | 1 point for the emergence of nodules |
| 4. Front paws | 0.5 point for each paw in which at least one inflammation appears on a joint |
| 5. Hind paws | 1 point for slight inflammation (swelling) 2 points for a medium-strength inflammation 3 points for a massive inflammatory reaction |

Animals forming a control group are only given the solvent (1% carboxymethyl cellulose in water). 6 animals are used for each dose and in the control group. A reduction in the increase in paw volume and a decrease in the arthritis index, as compared with the untreated control group, are used as the criteria for an effect having been achieved.

Table 1 shows the results. The total quantity of compounds 1 and 2 is constant in each of the different experiments.

TABLE 1

| Compound 1 (mg/kg of rat) | Compound 2 (mg/kg of rat) | Decrease in paw volume (%) | Decrease in arthritis index (%) |
|---|---|---|---|
| 10 | 0 | 74 | 58 |
| 9.9 | 0.1 | 93 | 66 |

TABLE 1-continued

| Compound 1 (mg/kg of rat) | Compound 2 (mg/kg of rat) | Decrease in paw volume (%) | Decrease in arthritis index (%) |
| --- | --- | --- | --- |
| 9.7 | 0.3 | 94 | 71 |
| 9.0 | 1.0 | 95 | 66 |
| 5 | 0 | 10% increase | 12% increase |
| 4.85 | 0.15 | 10 | 5 |
| 4.5 | 0.5 | 46 | 35 |

Both at 5 mg/kg and at 10 mg/kg of rat live weight, the effect of the novel preparation is markedly intensified by increasing quantities of compound 2. Therefore, small additional quantities of compound 2 lead to a marked intensification of the effect of the novel preparation.

The invention claimed is:

1. A solid composition comprising:
   a first component comprising 5-methyl-4'-trifluoromethyl-4-isoxazolecarboxanilide;
   a second component comprising a compound of formula I

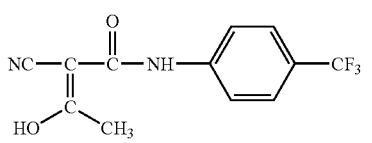

(I)

or a stereoisomeric form of the compound of formula I, or a physiologically tolerated salt of the compound of formula I; and
   a third component comprising a pharmaceutically tolerated excipient;
   wherein the first component has a concentration from about 2 to about 20 mg and the second component has a concentration from about 0.3% to about 15% of the first component.

2. The composition as claimed in claim 1, wherein the concentration of the second component is from about 1% to about 10% of the first component.

3. The composition as claimed in claim 1, wherein the concentration of the second component is from about 1% to about 5% of the first component.

4. The composition as claimed in claim 1, which comprises a first component and a second component in a form for rectal or oral administration.

5. The composition as claimed in claim 1, wherein the concentration of the second component is from about 0.5 % to about 15 % of the first component.

6. The composition as claimed in claim 1, wherein the concentration of the second component is from about 0.8 % to about 15 % of the first component.

7. A process for the preparation of a pharmaceutical composition of claim 1, which comprises processing components 1, 2, and 3 into a pharmaceutically acceptable form for administration.

8. A method of treating an immunological disease comprising administering to a patient in need of such treatment, a therapeutically effective amount of a solid composition comprising
   a first component comprising 5-methyl-4'-trifluoromethyl-4-isoxazolecarboxanilide;
   a second component comprising a compound of formula I

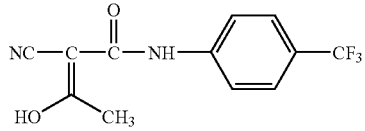

or a sterioisomeric form of the compound of formula I, or a physiologically tolerated salt of the compound of formula I; and
   a third component comprising a pharmaceutically tolerated excipient;
   wherein the first component has a concentration from about 2 to about 20 mg and the second component has a concentration from about 0.3% to about 15% of the first component.

9. The method of claim 6, wherein the composition produces a hyperadditive increase in the immunosuppressive effect.

10. A method according to claim 6, wherein the immunological disease is an acute immunological disease.

11. A method according to claim 8, wherein the acute immunological disease is sepsis, allergy, graft-versus-host reaction, or host-versus-graft reactions.

12. A method according to claim 6, wherein the immunological disease is an autoimmune disease.

13. A method according to claim 10, wherein the autoimmune disease is rheumatoid arthritis, systemic lupus erythrematosus, multiple sclerosis, psoriasis.

14. A method of treating a disease comprising administering to a patient in need of such treatment, a therapeutically effective amount of a solid composition comprising a first component comprising 5-methyl-4'-trifluoromethyl-4-isoxazolecarboxanilide;
   a second component comprising a compound of formula I

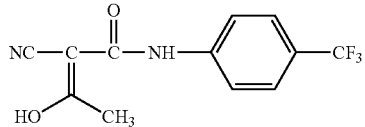

or a stereoisomeric form of the compound of formula I, or a physiologically tolerated salt of the compound of formula I; and
   a third component comprising a pharmaceutically tolerated excipient;
   wherein the first component has a concentration from about 2 to about 20 mg and the second component has a concentration from about 0.3% to about 15% of the first component, and wherein the disease is atopic dermatitis, asthma, urticaria, rhinitis, uveitis, type II diabetes, cystic fibrosis, colitis, or hepatic fibrosis.

* * * * *

UNITED STATES PATENT AND TRADEMARK OFFICE
CERTIFICATE OF CORRECTION

PATENT NO. : 7,071,222 B2
APPLICATION NO. : 09/101672
DATED : July 4, 2006
INVENTOR(S) : Robert Bartlett et al.

It is certified that error appears in the above-identified patent and that said Letters Patent is hereby corrected as shown below:

Claim 9, col. 6, line 24, "claim 6" should read --claim 8--.

Claim 10, col. 6, line 27, "claim 6" should read --claim 8--.

Claim 11, col. 6, line 30, "claim 8" should read --claim 10--.

Claim 12, col. 6, line 33, "claim 6" should read --claim 8--.

Claim 13, col. 6, line 35, "claim 10" should read --claim 12--.

Title page, item (73), "Assignee: Sanofi-Aventis Deuschland GmbH" should read --Assignee: Sanofi-Aventis Deutschland GmbH--.

Signed and Sealed this

Seventh Day of November, 2006

JON W. DUDAS
*Director of the United States Patent and Trademark Office*